(12) United States Patent
Shima et al.

(10) Patent No.: US 10,220,120 B2
(45) Date of Patent: Mar. 5, 2019

(54) ALLOY FOR MEDICAL USE AND METHOD OF PRODUCING THE SAME

(71) Applicants: TANAKA KIKINZOKU KOGYO K.K., Tokyo (JP); Kyoto University, Kyoto-shi, Kyoto (JP)

(72) Inventors: Kunihiro Shima, Isehara (JP); Kenji Goto, Hiratsuka (JP); Yasushi Masahiro, Tokyo (JP); Asaka Ueno, Tokyo (JP); Hiroo Iwata, Kyoto (JP); Ryusuke Nakai, Kyoto (JP); Tomonobu Kodama, Kyoto (JP)

(73) Assignees: TANAKA KIKINZOKU KOGYO K.K., Tokyo (JP); KYOTO UNIVERSITY, Kyoto (JP)

( * ) Notice: Subject to any disclaimer, the term of this patent is extended or adjusted under 35 U.S.C. 154(b) by 619 days.

(21) Appl. No.: 14/898,794

(22) PCT Filed: Jan. 30, 2014

(86) PCT No.: PCT/JP2014/052071
§ 371 (c)(1),
(2) Date: Dec. 16, 2015

(87) PCT Pub. No.: WO2014/208114
PCT Pub. Date: Dec. 31, 2014

(65) Prior Publication Data
US 2016/0367729 A1    Dec. 22, 2016

(30) Foreign Application Priority Data

Jun. 26, 2013 (JP) ................................. 2013-133459

(51) Int. Cl.
| | |
|---|---|
| C22C 1/02 | (2006.01) |
| A61L 29/02 | (2006.01) |
| A61L 31/02 | (2006.01) |
| C22C 5/02 | (2006.01) |
| C22F 1/00 | (2006.01) |
| C22F 1/14 | (2006.01) |
| B22D 7/00 | (2006.01) |
| B22D 21/00 | (2006.01) |

(52) U.S. Cl.
CPC ............. *A61L 29/02* (2013.01); *A61L 31/022* (2013.01); *B22D 7/005* (2013.01); *B22D 21/005* (2013.01); *C22C 1/02* (2013.01); *C22C 5/02* (2013.01); *C22F 1/00* (2013.01); *C22F 1/14* (2013.01)

(58) Field of Classification Search
CPC ........................................................ C22C 1/02
See application file for complete search history.

(56) References Cited

U.S. PATENT DOCUMENTS

| | | | | |
|---|---|---|---|---|
| 3,390,981 A | * | 7/1968 | Hoffman | A21D 6/003 75/351 |
| 2002/0168538 A1 | * | 11/2002 | Ellis | C22C 5/02 428/567 |
| 2006/0178260 A1 | * | 8/2006 | Zhong | B22F 9/24 502/185 |

FOREIGN PATENT DOCUMENTS

| | | |
|---|---|---|
| JP | 2004-505651 A | 2/2004 |
| JP | 4520944 B2 | 8/2010 |
| JP | 2010-536491 A | 12/2010 |
| WO | WO 2004/090180 A1 | 10/2004 |
| WO | WO 2010/084948 A | 7/2010 |

OTHER PUBLICATIONS

International Search Report PCT/JP2014/052071, dated Apr. 22, 2014.
Extended Search Report for EP Application No. 14817991.4, dated Apr. 12, 2017.

* cited by examiner

*Primary Examiner* — Christopher S Kessler
(74) *Attorney, Agent, or Firm* — Orrick, Herrington & Sutcliffe LLP; Joseph A. Calvaruso

(57) ABSTRACT

The present invention is an alloy for medical use including an Au—Pt alloy, containing 34 to 36 mass % of Pt with the balance being Au, and having an α-phase single structure in which a ratio of a peak intensity (X) of a Pt (111) plane to a peak intensity (Y) of an Au (111) plane (X/Y) is 0.01 or less in an X-ray diffraction analysis. The alloy can be produced in such a manner that after the Au—Pt alloy ingot is molten and cast, cold working and a heat treatment for homogenization are performed at least two times on the molten and cast alloy. The alloy of the present invention is an artifact-free material that exhibits excellent compatibility with a magnetic field environment such as an MRI and has magnetic susceptibility of ±4 ppm with respect to that of water.

8 Claims, 5 Drawing Sheets

Gradient Echo IMAGE (Cornal)

Au76Pt24  Au74Pt26  Au72Pt28  Au71Pt29  Au705Pt295  Au70Pt30

Au69Pt31  Au68Pt32  Au67Pt33  Au66Pt34  Au65Pt35  Au64Pt36

Spin Echo IMAGE (Cornal)

Au76Pt24  Au74Pt26  Au72Pt28  Au71Pt29  Au705Pt295  Au70Pt30

Au69Pt31  Au68Pt32  Au67Pt33  Au66Pt34  Au65Pt35  Au64Pt36

ALLOY FOR MEDICAL USE AND METHOD OF PRODUCING THE SAME

TECHNICAL FIELD

The present invention relates to an alloy for medical use, specifically to an alloy suitable for a medical appliance such as an embolus treatment coil, and more specifically, to an alloy in which an artifact (false image) hardly occurs in a magnetic field environment such as a magnetic resonance image diagnosis apparatus (MRI).

BACKGROUND ART

A material for medical use applied to a medical appliance such as an embolus treatment coil, a clip, a catheter, a stent, or a guide wire requires characteristics such as biocompatibility, corrosion resistance, and workability. Regarding these requirements, for example, stainless, a Co—Cr alloy, and a Pt—W alloy have been practically used as a metal material (see Patent Document 1).

Recently, with the widespread of inspection and therapy using a magnetic resonance image diagnosis apparatus (MRI) in a medical practice, there is a growing concern over an influence on an interaction between constituent materials of the medical appliance and an electromagnetic field in a magnetic field environment. Examples of material characteristics considering the magnetic field environment include magnetic susceptibility. The magnetic susceptibility of the material is problematic because it can be a factor of an artifact of the MRI. The artifact due to the magnetic susceptibility magnetizes a metal in a magnetic field to cause distortion or the like of an MRI image in a peripheral region of the magnetic field. The occurrence of the artifact hinders accurate surgery and diagnostic. The material for medical use with practical examples has high magnetic susceptibility and thus cannot suppress the artifact.

There are a small number of development examples of an alloy in consideration of an artifact-free. For example, Patent Document 2 discloses a development example of a stent which is applied with an Au—Pd alloy or an Ag—Pd alloy and is compatible with the MRI.

RELATED ART DOCUMENT

Patent Documents

Patent Document 1: JP 2010-536491 A
Patent Document 2: JP 4523179 B2

SUMMARY OF THE INVENTION

Problems to be Solved by the Invention

However, the conventional alloys are made with merely lowering magnetic susceptibility taken into consideration and a criterion of the magnetic susceptibility is obscure. According to the present inventors, these alloys are not actually considered as an artifact-free material.

Here, the embodied criteria required for a material capable of achieving the artifact-free is that the magnetic susceptibility (volume magnetic susceptibility) of the material is approximate to that of a biopsy tissue. Since the magnetic susceptibility of the biopsy tissue results from water as a main constituent, and the magnetic susceptibility of the water is −9 ppm (−9×10$^{-6}$), the magnetic susceptibility of the biopsy tissue exhibits a slight diamagnetism. Accordingly, the magnetic susceptibility of the artifact-free material is approximate to the magnetic susceptibility (−9 ppm) of the water.

The present invention has been made in view of the above circumstances and provides an alloy material with excellent compatibility with a magnetic field environment such as an MRI and can achieve an artifact-free material. As the specific criterion, the magnetic susceptibility (−13 to −5 ppm) of ±4 ppm with respect to that of the water is applied.

Means for Solving the Problems

As described above, the present invention provides an artifact-free alloy having magnetic susceptibility (volume magnetic susceptibility) from −13 ppm to −5 ppm, but this target value indicates slight diamagnetism. Accordingly, the present inventors applied Au as a metal element serving as a base of such a diamagnetic alloy. The reason is that Au is a diamagnetic metal having magnetic susceptibility of −34 ppm and is also excellent in biocompatibility, corrosion resistance, workability or the like, thereby being suitable for a material for medical use. Then, the present inventors have alloyed metals having positive magnetic susceptibility to make the magnetic susceptibility of Au the target value. These alloy elements require the positive magnetic susceptibility as well as biocompatibility and corrosion resistance similarly to Au. The present inventors applied Pt as the alloy element. The reason is that Pt is a metal having magnetic susceptibility of +279 ppm and has the requirement characteristics. Additionally, Pt is also easily alloyed with Au and can produce a single phase alloy consisting of only an α-phase being a supersaturated solid solution.

The present inventors examined the change in magnetic susceptibility of an Au—Pt alloy while adjusting compositions of the Au—Pt alloy. As a result, they have confirmed that the magnetic susceptibility tends to change into a positive value as the amount of Pt to be added increases. However, there are problems that the Au—Pt alloy produced by a general production process has poor reproducibility of the magnetic susceptibility and the magnetic susceptibility of the alloy has a large gap with the target magnetic susceptibility (−13 to −5 ppm) even when the magnetic susceptibility has a tendency as described above. Here, after further examining these problems, the present inventors have focused on the presence of a small amount of precipitates in the alloy.

That is, the Au—Pt alloy indicates a phase diagram (FIG. 1) with a homogeneous solid-solution type and can obtain a single-phase alloy of an α-phase by a solution treatment from an α-phase region. However, a small amount of Pt-rich α$_2$-phase may precipitate from the α-phase during the solution treatment. The present inventors consider that the magnetic susceptibility locally and significantly varies even when an amount of such precipitates is small and that reproducibility of the magnetic susceptibility decreases when the precipitates exist in a random manner.

Therefore, the present inventors performed extensive examination including a review of production processes under such a consideration to find a tolerable amount of precipitates and an alloy composition capable of exerting stably the target magnetic susceptibility, and conceived the present invention.

Specifically, the present invention provides an alloy for medical use including an Au—Pt alloy, wherein the alloy contains 34 to 36 mass % of Pt with the balance being Au, and has an α-phase single structure in which a ratio of a peak intensity (X) of a Pt (111) plane to a peak intensity (Y) of an Au (111) plane (X/Y) is 0.01 or less in an X-ray diffraction analysis.

The present invention will be described in more detail below. As described above, the present invention defines the alloy composition (Pt content) and the peak intensity originating from the precipitates in an X-ray diffraction analysis for the Au—Pt alloy.

First, with respect to the alloy composition, the content of Pt is 34 to 36 mass % and the balance is Au, as the magnetic susceptibility of the alloy is within an appropriate range based on the magnetic susceptibility of each of Au and Pt on the premise that the composition is adjusted to the above range. When the content of Pt is less than 34 mass %, the magnetic susceptibility indicates a lower value than a lower limit value (−13 ppm) of the target magnetic susceptibility even if the precipitates are completely eliminated and the phase structure of the alloy is made a single phase. Additionally, even when the content of Pt exceeds 36 mass %, only an alloy having magnetic susceptibility exceeding an upper limit value (−5 ppm) of the target magnetic susceptibility is produced.

In the present invention, the ratio of a peak intensity (X) of a Pt (111) plane to a peak intensity (Y) of an Au (111) plane (X/Y) is defined to be 0.01 or less in the X-ray diffraction analysis. The definition intends to set the upper limit of a tolerable amount of precipitates ($\alpha_2$-phase) in the alloy. As described above, the presence of the precipitates greatly varies the magnetic susceptibility of the alloy. Furthermore, the precipitates usually tend to precipitate in the vicinity of grain boundaries, but still precipitate in a random manner. As a result, the reproducibility of the magnetic susceptibility of the alloy is impaired. Therefore, the present invention strictly regulates the amount of precipitates.

The present invention applies a peak of the Pt (111) plane in the X-ray diffraction analysis to identify the Pt-rich phase serving as a precipitate in the alloy. This peak originates from the $\alpha_2$-phase (Pt-rich phase) serving as a precipitate and appears in the vicinity of a value of 2θ=39.2° to 39.3°. Then, a peak (2θ=38.3° near) of the Au (111) plane is applied to the peak intensity of the Pt (111) plane as a criteria. The peak of the Au (111) plane originates from the α-phase serving as a mother phase of the alloy. The amount of precipitates is specified by these peak ratios. The peak of the Au (111) plane often appears as a main peak in the X-ray diffraction analysis for the alloy of the present invention, but does not necessarily become a main peak. For example, a peak of an Au (200) plane appearing in the vicinity of 44.5° may become a main peak.

When the peak intensity ratio exceeds 0.01, the result indicates that the amount of precipitates is present enough to have an adverse influence on the magnetic susceptibility. Accordingly, the peak intensity ratio is preferably 0 (zero), and this case is in a state of a perfect α-single phase.

Here, as described above, the Au—Pt alloy of the present invention regulates the amount of precipitates (Pt-rich phase) and is made into an alloy of the α-single phase, but the uniformity of this structure phase also leads to compositional uniformity. The significance of compositional uniformity is to have a uniform state where the concentration distribution of Pt has no deviation by a site in a bulk-like alloy.

Specifically, for example, the deviation of Pt concentration is 3% or less between the central portion and the peripheral portion of the alloy. The alloy having the above composition range and having less deviation of the Pt concentration is suitable for an artifact-free medical material in that the magnetic susceptibility is uniform. The deviation of the Pt concentration is more preferably 2% or less.

Next, a method of producing an alloy for medical use including an Au—Pt alloy of the present invention will be described. As described above, the Au—Pt alloy of the present invention has the uniformity of the structure phase called the α-single phase in which the precipitates are regulated and can have the compositional uniformity. The method of producing the alloy generally includes a melting and casting process as a starting point and a thermomechanical treatment such as forging, rolling, or a heat treatment. However, in the production of an extremely homogenized alloy material as in the present invention, it is necessary to take an appropriate action to inhibition factors of the homogenization such as segregation or phase separation which may occur in each of these processes.

For example, the segregation occurs in the melting and casting process, and so-called macro-segregation and micro-segregation compositionally inhibit homogeneity. In this regard, the macro-segregation can be eliminated by the forging after the casting and the heat treatment, but relatively minute segregation due to the micro-segregation is not also ignored in the present invention. The micro-segregation tends to occur by a residual solidification structure (dendrite structure) during the casting.

Additionally, the phase separation due to formation of precipitates occurs during the thermomechanical treatment. The Au—Pt alloy of α-single phase can be produced by the solution treatment to form Pt as a solid solution in a supersaturated manner, after the alloy is heated to the α-phase region temperature. However, in the production of the alloy formed as a solid solution in such a non-equilibrium state, the separation of a phase ($\alpha_2$-phase) which can occur in an equilibrium state, slightly occurs.

The present inventors examined while considering these inhibition factors of the homogeneity and found a method of producing an Au—Pt alloy, which has no segregation and remarkably reduced precipitates, by performing a predetermined homogenizing treatment on an alloy ingot obtained after the melting and casting. The method of producing the alloy for medical use includes: melting and casting an alloy ingot comprised of an Au—Pt alloy containing 34 to 36 mass % of Pt with the balance being Au; and subsequently performing, at least twice, a homogenizing treatment including a cold working process of the alloy ingot and a heat treatment process of heating the cold-worked alloy ingot to 1150 to 1250° C. and then rapidly cooling the heated alloy ingot.

In the present invention, the homogenizing treatment includes a set of a process of performing cold working on the molten cast alloy ingot and a process of performing the heat treatment on the worked ingot to the α-phase region temperature or higher depending on the composition, and these processes are required to be performed several times. The heat treatment intends to make the phase structure of the alloy be the α-phase, and return a small amount of generated precipitates to the α-phase to finally eliminate the precipitates when the heat treatment is performed several times. Additionally, the cold working intends to destroy a cast structure by melting and casting, resulting in eliminating segregation, and repetition of the cold working can make a material composition uniform.

Examples of the cold working in the homogenizing treatment may include any of working ways such as cold rolling, cold forging, cold drawing, or cold extrusion. The cold rolling is preferred. The working ratio in the cold working is preferably 30% or more. This is for sufficiently accumulating lattice defects (for example, transition) which act as a driving force of atomic diffusion for homogenization. Incidentally, a working temperature of the cold working is preferably a room temperature, because an $\alpha_2$-phase may precipitate during warm working or hot working.

The heat treatment in the homogenizing treatment is preferably performed at a heating temperature of 1150 to 1250° C. to form the α-single phase region. A heating time is preferably set to be 1 to 24 hours. Moreover, it is preferable to promptly put the alloy into a cooling medium to rapidly cool it, after the heating. During the rapid cooling, it is preferable to cool the alloy within three seconds after taken out from a furnace, to suppress the precipitation of the $\alpha_2$-phase during the temperature drop of the alloy until the alloy is put into the cooling medium.

The homogenizing treatment including the cold working and the heat treatment as described above is performed twice or more. This is because effects are insufficient in one-time homogenizing treatment and thus an alloy having suitable magnetic susceptibility cannot be produced.

General melting and casting conditions can be applied to the melting and casting process before the homogenizing treatment. The composition of the alloy is adjusted by mixing each of an Au metal and a Pt metal to a target composition (Pt: 34 to 36 mass %), and the mixture can be molten and cast by arc melting, high-frequency heating melting or the like to produce an alloy ingot.

The molten and cast alloy ingot is preferably subjected to hot forging before the homogenizing treatment. Fracture of the solidification structure and a segmentation of segregation previously performed by the hot forging with less deformation resistance make the following homogenizing treatment more effective. A working temperature at this time is preferably 700 to 1050° C., because forgeability of the alloy is insufficient and thus cracks may occur during the forging when the working temperature is lower than 700° C.

The production process having the homogenizing treatment described above can produce the homogenized Au—Pt alloy having no precipitates or segregation. The Au—Pt alloy subjected to the homogenizing treatment has no shape limitation and can be formed into various shapes according to use by plastic working, for example, a wire rod, a bar, a plate, and a tube. Furthermore, the alloy can be made into a target shape using the cold working in the homogenizing treatment. For example, a plate and a wire rod can be directly produced using rolling and groove rolling instead of the cold working during the homogenizing treatment.

Advantageous Effects of the Invention

As described above, an alloy for medical use including an Au—Pt alloy of the present invention has magnetic susceptibility suitable for an artifact-free material. From the constituent elements, the characteristics such as biocompatibility, corrosion resistance, or workability required for the alloy for medical use are also excellent. The present invention is suitable for the medical appliance such as an embolus treatment coil and is useful in the medical appliance used in a magnetic field environment such as an MRI.

DESCRIPTION OF EMBODIMENTS

Figure 1:
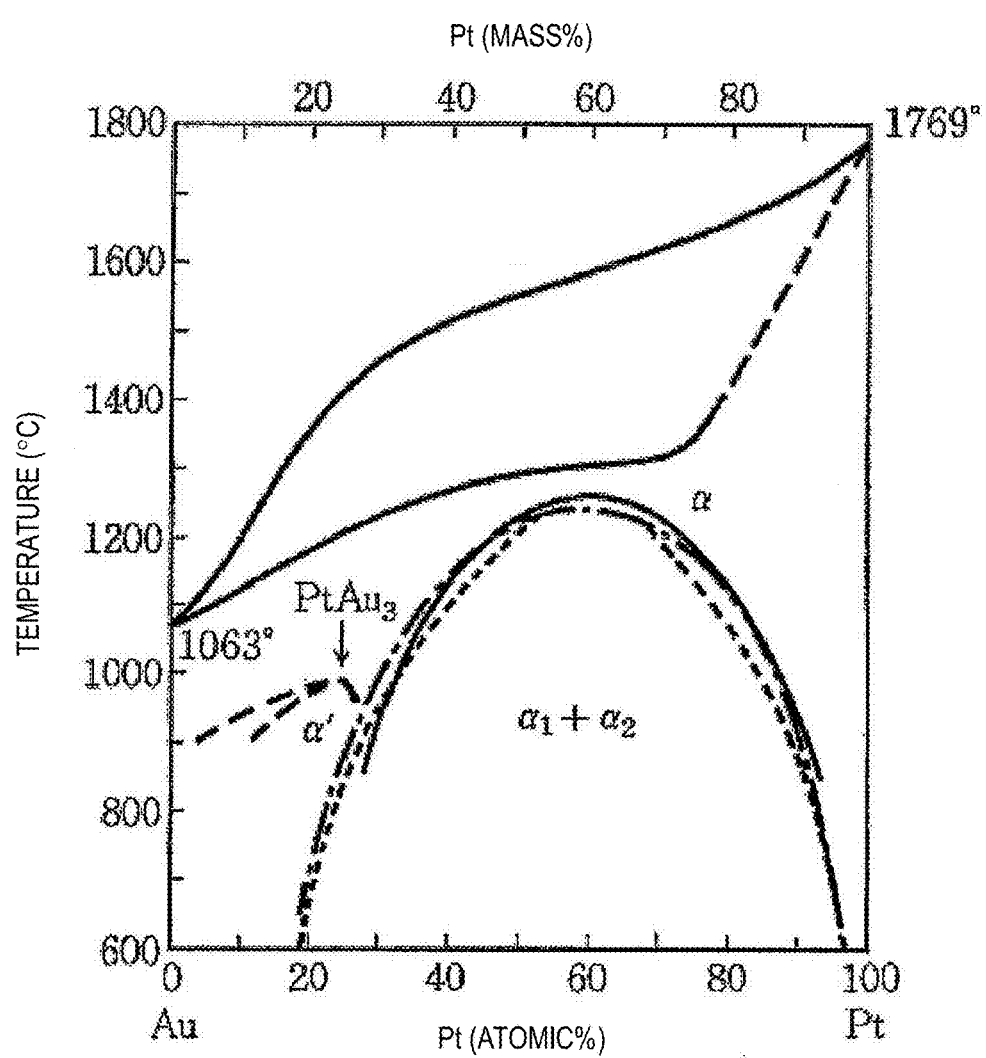
FIG. 1 is a phase diagram of an Au—Pt alloy.

An embodiment of the present invention will be described below. In the present invention, magnetic susceptibility measurement and probability of artifact occurrence were examined after producing an Au—Pt alloy with varying Pt concentration and confirming a phase structure and composition distribution of the Au—Pt alloy. A process of producing the Au—Pt alloy is as follows.

Pure Au and pure Pt (both having purity of 99.99%: produced by Tanaka Kikinzoku Kogyo K. K.) were weighed to be a target composition and were subjected to high-frequency melting, whereby an alloy ingot was cast. The alloy ingot of about 60 g was produced. The molten and cast alloy ingot was subjected to hot forging. The hot forging was performed at 1000° C.

Subsequently, the alloy ingot was subjected to a homogenizing treatment. As the homogenizing treatment, first, the alloy ingot was subjected to cold groove rolling and then to cold working (working ratio: 40%). Then, the alloy ingot was heated for one hour at 1200° C. Thereafter, the alloy was introduced into ice water to be rapidly cooled. The homogenizing treatment, which was a combination of the cold working and the heat treatment, was performed three times in the present embodiment. The homogenized alloy was thus subjected to groove rolling to produce an Au—Pt alloy wire. In the present embodiment, the Au—Pt alloy wire having Pt concentration of 24 to 36 mass % was produced.

In the present embodiment, the Au—Pt alloy was produced even in production conditions in which precipitates could occur. That is, the molten and cast alloy ingot was subjected to homogenizing treatment only once in the production process, and then worked into the wire. The comparison samples were also produced for Au—Pt alloys having multiple compositions.

First, an X-ray diffraction analysis and a composition analysis of a cross-section were performed on the produced Au—Pt alloy wire. The X-ray diffraction analysis was performed by measuring a measurement plane at a measurement speed of 0.2°/sec using a CuKα ray (45 kV, 40 mA) as an X-ray source, the measurement plane being a cross-section vertical to a longitudinal direction of the Au—Pt alloy wire. Additionally, the composition analysis of the cross-section was performed by setting a plurality of measurement points to perform an EDX analysis during SEM observation on the cross-section of the Au—Pt alloy wire.

Subsequently, the magnetic susceptibility of each alloy was measured. The magnetic susceptibility measurement was performed on each of the alloy samples by use of a magnetic characteristic measuring apparatus (7T-SQUID (superconducting quantum interference element) fluxmeter manufactured by Quantum Design, Inc.). A measurement temperature was 37° C. Additionally, the presence of the artifact was evaluated using an MRI apparatus (Magnetom Sonata 1.5T manufactured by Siemens Inc.). This evaluation was performed by imaging the alloy sample fixed with an agarose gel in a Pyrex (registered trademark) test tube (ϕ 3.5 mm) using the MRI apparatus and visually confirming whether the artifact is present or not. A gradient echo method (TR: 270 ms, TE: 15 ms) and a spin echo method (TR: 500 ms, TE: 20 ms) were used for image taking.

Figure 2:
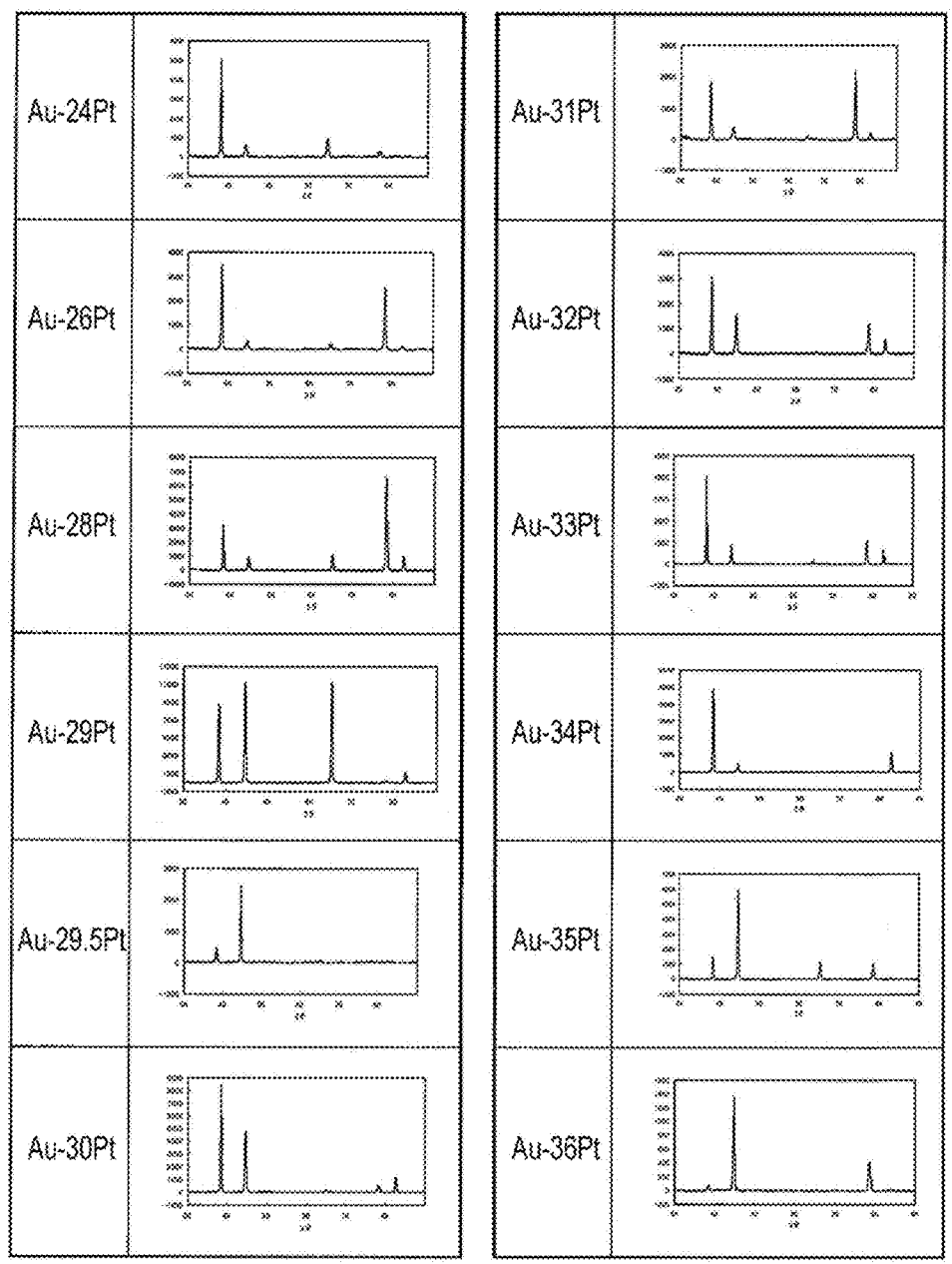
FIG. 2 is a diagram illustrating XRD pattern of each of Au—Pt alloy samples.
Figure 3:
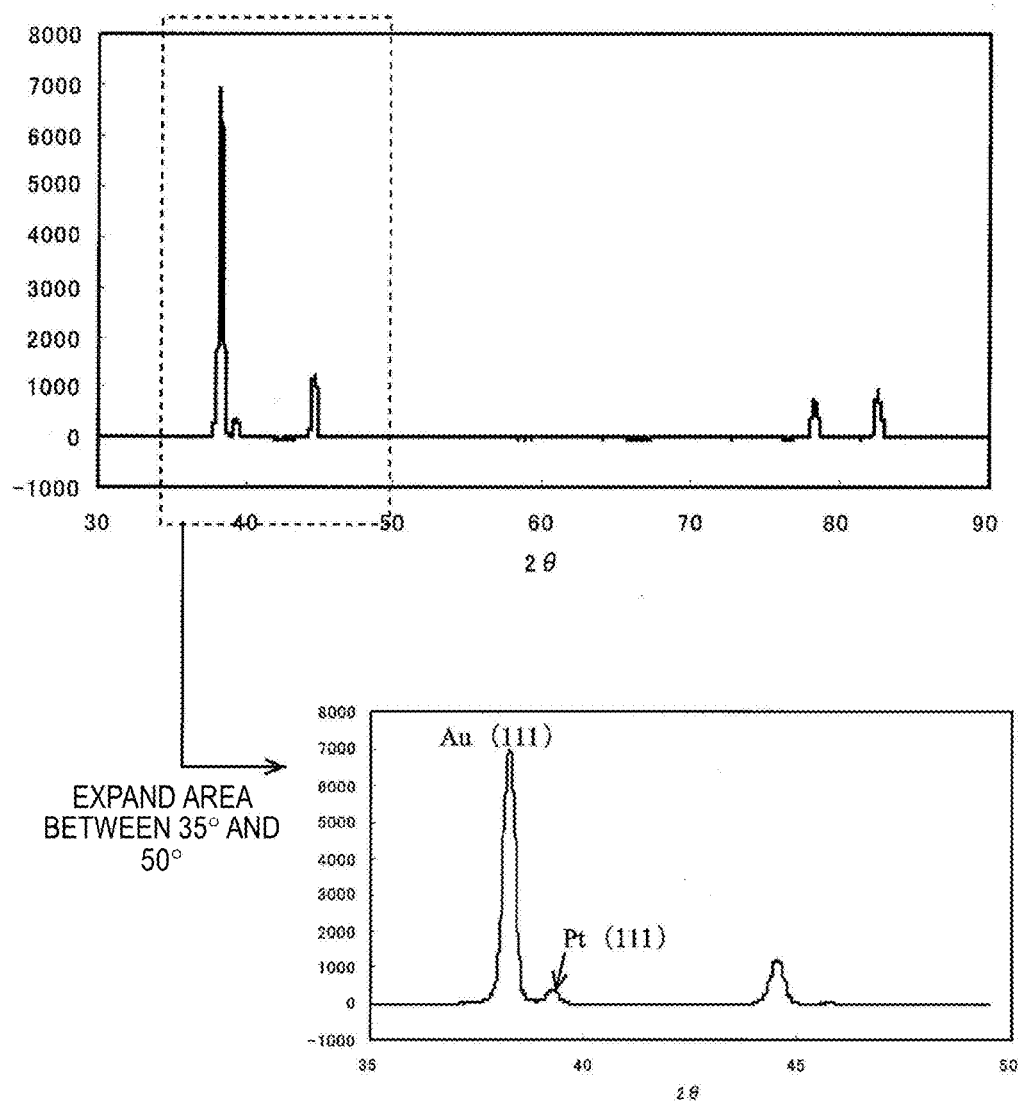
FIG. 3 is a diagram illustrating an XRD pattern of an Au—Pt alloy which is subjected to homogenizing treatment only once.

FIG. 2 illustrates XRD patterns of each of the alloy samples. In FIG. 2, a peak of Pt (111) plane was not observed for the Au—Pt alloy subjected to the proper number of times of homogenizing treatment. An intensity ratio to a peak of Au (111) plane becomes zero. In contrast, FIG. 3 illustrates an XRD pattern of an alloy subjected to only one homogenizing treatment, a peak of Pt (111) plane is observed although it is weak. At this time, a peak intensity ratio was 0.05. The peak of the Pt (111) plane was considered to be due to the fact that the homogenizing treatment was insufficient and thus an $\alpha_2$-phase could not be completely eliminated.

Additionally, Table 1 indicates results obtained by performing an EDX analysis on multiple points toward both ends through the center of the cross-section of each of the alloy samples to analyze Pt concentration and measuring the maximum Pt concentration and the minimum Pt concentration. The alloy sample produced at this time was homogeneous in which no precipitate was observed also from the SEM observation, and the Pt concentration difference was 2 mass % or less. Accordingly, The Pt concentration was found to be substantially uniform over the cross-section for each alloy produced under suitable production conditions of which the homogenizing treatment was repeatedly performed several times.

TABLE 1

| Composition | Pt concentration difference (mass %) |
|---|---|
| Au—24 Pt | 1.78% |
| Au—26 Pt | 1.05% |
| Au—28 Pt | 1.69% |
| Au—29 Pt | 1.22% |
| Au—29.5 Pt | 1.00% |
| Au—30 Pt | 1.25% |
| Au—31 Pt | 1.21% |
| Au—32 Pt | 1.30% |
| Au—33 Pt | 1.54% |
| Au—34 Pt | 1.33% |
| Au—35 Pt | 1.05% |
| Au—36 Pt | 1.65% |

Figure 4:
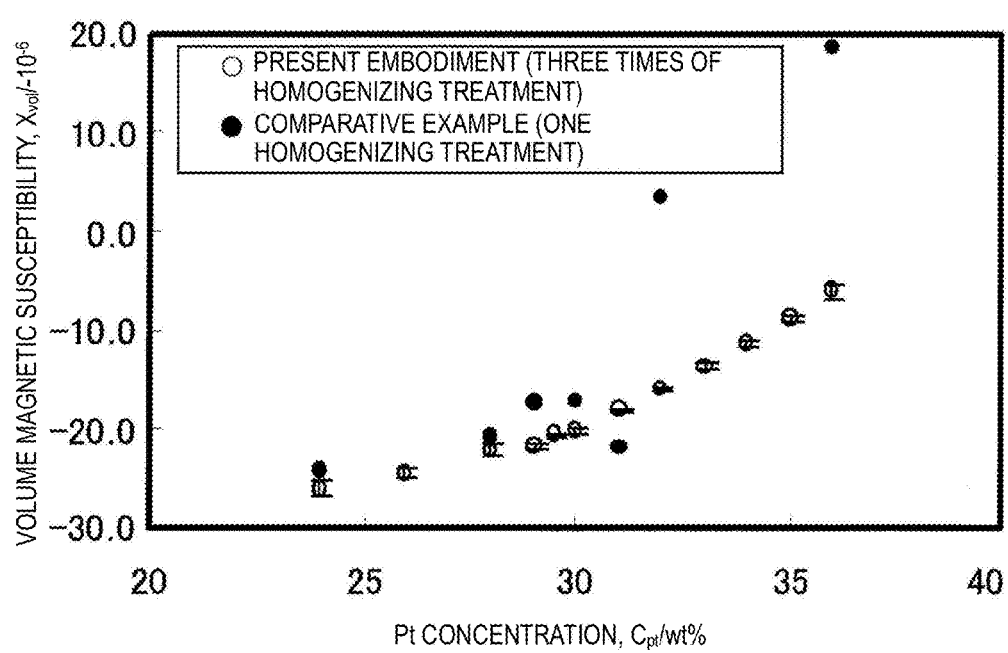
FIG. 4 is a diagram illustrating measurement results of magnetic susceptibility of each of Au—Pt alloy samples.

FIG. 4 illustrates measurement results of magnetic susceptibility of each of the alloy samples. FIG. 4 shows that the magnetic susceptibility monotonously increased to a positive value with an increase of the Pt concentration in Au—Pt alloy produced by several repetitive homogenizing treatments. When the Pt concentration is 34 to 36 mass %, the magnetic susceptibility is ±4 ppm relative to that of water and the magnetic susceptibility of −13 ppm to −5 ppm is confirmed to be exhibited.

Meanwhile, for an alloy with insufficient homogenization, the magnetic susceptibility tends to increase toward the positive value to some extent with the increase of the Pt concentration. However, the value does not monotonously increase, but is jumped and becomes discontinuous in the vicinity of a preferred value. Even when the Pt concentration is 34 to 36 mass %, the magnetic susceptibility does not indicate a preferred value. Accordingly, to control the magnetic susceptibility to the preferred value, it is necessary to optimize the phase structure as well as the composition (Pt concentration).

Figure 5:
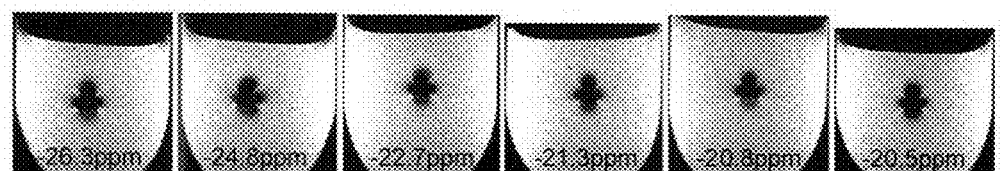
FIG. 5 shows imaging results of each of Au—Pt alloy samples by an MRI apparatus.
Figure 5:
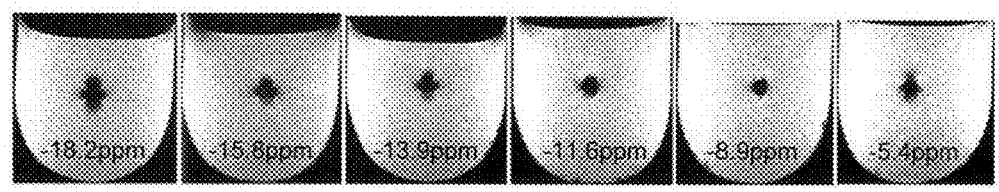
Figure 5:
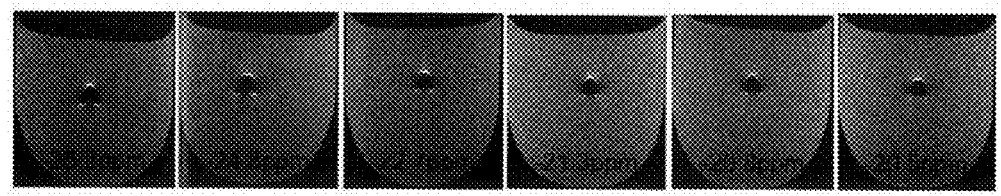
Figure 5:
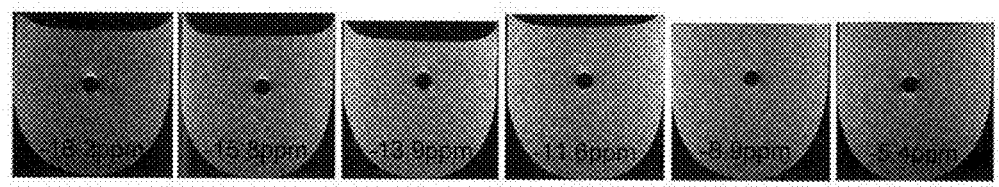

FIG. 5 shows imaging results of the homogenized Au—Pt alloy by the MRI apparatus used to confirm the presence or absence of the artifact occurrence. When these results are examined while the above results of the magnetic susceptibility are compared, the artifact is confirmed to have occurred in an alloy having the Pt concentration of 32% or less from spin echo images. Furthermore, the artifact is confirmed to have occurred in an alloy having the Pt concentration of 33% or less from gradient echo images. The artifact is easily observed by the gradient echo method compared to the spin echo method, and this tendency is also seen from the results in FIG. 5. Accordingly, the artifact-free Au—Pt alloy preferably has the Pt concentration from 34% or more to 36% or less.

INDUSTRIAL APPLICABILITY

An alloy for medical use including an Au—Pt alloy of the present invention has suitable magnetic susceptibility to suppress an artifact. This alloy has also excellent characteristics such as biocompatibility, corrosion resistance, or workability required for the alloy for medical use. The present invention is useful for a medical appliance such as an embolus treatment coil, a clip, a catheter, a stent, or a guide wire and for a medical appliance to be used in a magnetic field environment such as an MRI.

The invention claimed is:

1. An alloy for medical use comprising an Au—Pt alloy, wherein the alloy contains 34 to 36 mass % of Pt with the balance being Au, and has an α-phase single structure in which a ratio of a peak intensity (X) of a Pt (111) plane to a peak intensity (Y) of an Au (111) plane (X/Y) is 0.01 or less in an X-ray diffraction analysis, and wherein the alloy has a volume magnetic susceptibility of from −13 ppm to −5 ppm.

2. A method of producing an alloy for medical use, the alloy defined in claim 1, comprising the steps of:
    melting and casting an alloy ingot comprising an Au—Pt alloy containing 34 to 36 mass % of Pt with the balance being Au; and
    performing, at least twice, a homogenizing treatment including a cold working process of the alloy ingot and a heat treatment process of heating the cold-worked alloy ingot to 1150 to 1250° C. and then rapidly cooling the heated alloy ingot.

3. The method of producing the alloy for medical use according to claim 2, wherein the cold working of the homogenizing treatment sets a working ratio to be 30% or more.

4. The method of producing the alloy for medical use according to claim 2, wherein the heat treatment process of the homogenizing treatment effects heating the alloy ingot to 1150 to 1250° C. for at least one hour and then rapidly cooling the heated alloy ingot.

5. The method of producing the alloy for medical use according to claim 2, wherein the molten and cast alloy ingot is subjected to hot forging before the homogenizing treatment.

6. The method of producing the alloy for medical use according to claim 3, wherein the heat treatment process of the homogenizing treatment effects heating the alloy ingot to 1150 to 1250° C. for at least one hour and then rapidly cooling the heated alloy ingot.

7. The method of producing the alloy for medical use according to claim 3, wherein the molten and cast alloy ingot is subjected to hot forging before the homogenizing treatment.

8. The method of producing the alloy for medical use according to claim 4, wherein the molten and cast alloy ingot is subjected to hot forging before the homogenizing treatment.

* * * * *